(12) United States Patent
Donhowe et al.

(10) Patent No.: US 11,791,032 B2
(45) Date of Patent: Oct. 17, 2023

(54) SYSTEMS AND METHODS FOR FILTERING LOCALIZATION DATA

(71) Applicant: INTUITIVE SURGICAL OPERATIONS, INC., Sunnyvale, CA (US)

(72) Inventors: Caitlin Q. Donhowe, Mountain View, CA (US); Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 409 days.

(21) Appl. No.: 16/802,109

(22) Filed: Feb. 26, 2020

(65) Prior Publication Data

US 2020/0188038 A1 Jun. 18, 2020

Related U.S. Application Data

(63) Continuation of application No. 15/525,909, filed as application No. PCT/US2015/060083 on Nov. 11, 2015, now abandoned.
(Continued)

(51) Int. Cl.
*A61B 34/30* (2016.01)
*G16H 20/40* (2018.01)
(Continued)

(52) U.S. Cl.
CPC ............. *G16H 20/40* (2018.01); *A61B 34/10* (2016.02); *A61B 34/20* (2016.02); *A61B 34/30* (2016.02);
(Continued)

(58) Field of Classification Search
CPC .... A61B 2017/00809; A61B 2034/105; A61B 2034/107; A61B 2034/2051;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

JP 2001282848 A 10/2001
WO WO-2011100110 A1 8/2011
(Continued)

OTHER PUBLICATIONS

Extended European Search Report for Application No. EP15858691.7, dated Jun. 12, 2018, 9 pages (ISRG06240/EP).
(Continued)

*Primary Examiner* — Christopher L Cook
(74) *Attorney, Agent, or Firm* — HAYNES AND BOONE, LLP

(57) ABSTRACT

A medical system comprises a medical instrument system and an assembly removably coupled to the medical instrument system. The assembly is configured to operate the medical instrument system by moving it within an anatomic passageway. The medical system also comprises a sensor system coupled to the instrument system and configured to generate information including spatial data and shape data about the instrument system. The medical system also comprises a control system communicatively coupled to the instrument system, the assembly, and the sensor system. The control system receives, from the sensor system, a first set of the spatial data including position information for a distal end of the medical instrument system during a plurality of time periods. The control system also receives the shape data
(Continued)

from the sensor system and filters the first set of the spatial data.

20 Claims, 8 Drawing Sheets

Related U.S. Application Data

(60) Provisional application No. 62/079,139, filed on Nov. 13, 2014.

(51) Int. Cl.
| | | |
|---|---|---|
| *G16H 40/63* | (2018.01) | |
| *G16H 30/40* | (2018.01) | |
| *A61B 34/10* | (2016.01) | |
| *A61B 34/20* | (2016.01) | |
| *A61B 34/35* | (2016.01) | |
| *A61B 90/00* | (2016.01) | |
| *A61B 17/00* | (2006.01) | |
| *A61B 34/00* | (2016.01) | |

(52) U.S. Cl.
CPC .............. *A61B 34/35* (2016.02); *G16H 30/40* (2018.01); *G16H 40/63* (2018.01); *A61B 34/76* (2016.02); *A61B 90/37* (2016.02); *A61B 2017/00809* (2013.01); *A61B 2034/105* (2016.02); *A61B 2034/107* (2016.02); *A61B 2034/2051* (2016.02); *A61B 2034/2061* (2016.02); *A61B 2034/2065* (2016.02); *A61B 2034/2072* (2016.02); *A61B 2034/301* (2016.02); *A61B 2090/064* (2016.02); *A61B 2090/371* (2016.02); *A61B 2090/373* (2016.02); *A61B 2090/374* (2016.02); *A61B 2090/376* (2016.02); *A61B 2090/3735* (2016.02)

(58) Field of Classification Search
CPC .... A61B 2034/2061; A61B 2034/2065; A61B 2034/2072; A61B 2034/301; A61B 2090/064; A61B 2090/371; A61B 2090/373; A61B 2090/3735; A61B 2090/374; A61B 2090/376; A61B 34/10; A61B 34/20; A61B 34/30; A61B 34/35; A61B 34/76; A61B 90/37; G16H 20/40; G16H 30/40; G16H 40/63
See application file for complete search history.

(56) References Cited

U.S. PATENT DOCUMENTS

| | | |
|---|---|---|
| 7,316,681 B2 | 1/2008 | Madhani et al. |
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 2006/0013523 A1 | 1/2006 | Childlers et al. |
| 2008/0071140 A1 | 3/2008 | Gattani et al. |
| 2008/0161668 A1 | 7/2008 | Wittkampf et al. |
| 2010/0030063 A1* | 2/2010 | Lee .................... A61B 5/06 600/424 |
| 2012/0029339 A1 | 2/2012 | Cohen |
| 2012/0165655 A1 | 6/2012 | Mucha |
| 2012/0289843 A1 | 11/2012 | Chopra et al. |
| 2013/0223702 A1 | 8/2013 | Holsing et al. |
| 2013/0303892 A1 | 11/2013 | Zhao et al. |
| 2014/0148808 A1* | 5/2014 | Inkpen ................ A61B 90/06 73/866.5 |
| 2014/0180063 A1 | 6/2014 | Zhao et al. |
| 2014/0187905 A1 | 7/2014 | Olson |
| 2015/0265368 A1 | 9/2015 | Chopra et al. |
| 2017/0325896 A1 | 11/2017 | Donhowe et al. |

FOREIGN PATENT DOCUMENTS

| | | |
|---|---|---|
| WO | WO-2012158324 A2 | 11/2012 |
| WO | WO-2014058838 A1 | 4/2014 |

OTHER PUBLICATIONS

International Preliminary Report on Patentability for Application No. PCT/US2015/060083, dated May 26, 2017, 7 pages (ISRG06240/PCT).
International Search Report and Written Opinion for Application No. PCT/US2015/060083, dated Feb. 18, 2016, 10 pages (ISRG06240/PCT).
Tomoda K., et al., "The Evaluation of Navigation Surgery in Nose and Paranasal Sinuses," in: Computer Assisted ENT Surgery, International Journal of Computer Assisted Radiology and Surgery, vol. 1(7), pp. 311-323, May 2006.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP22201322.9, dated Jan. 31, 2023, 09 pages.

\* cited by examiner

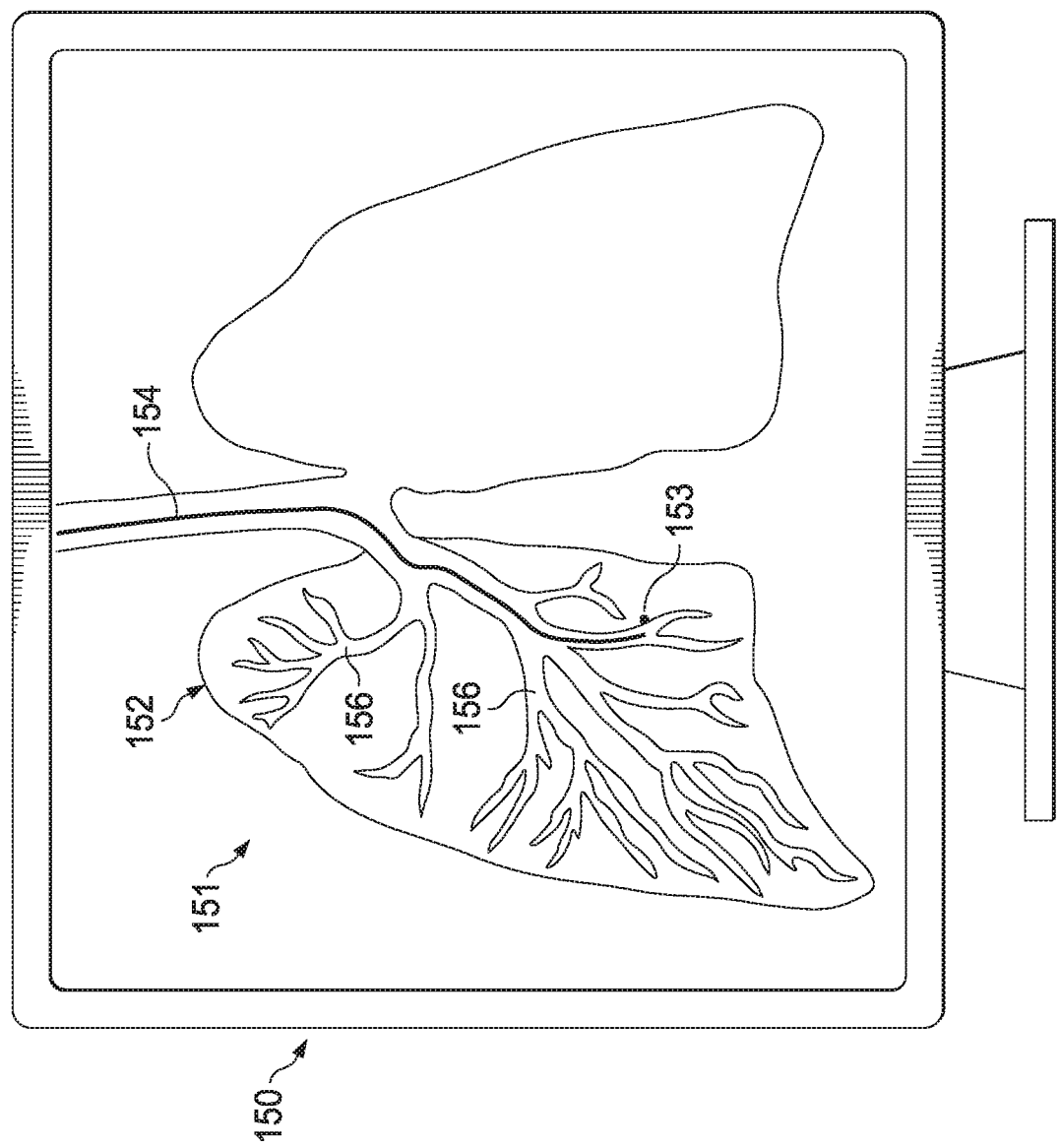

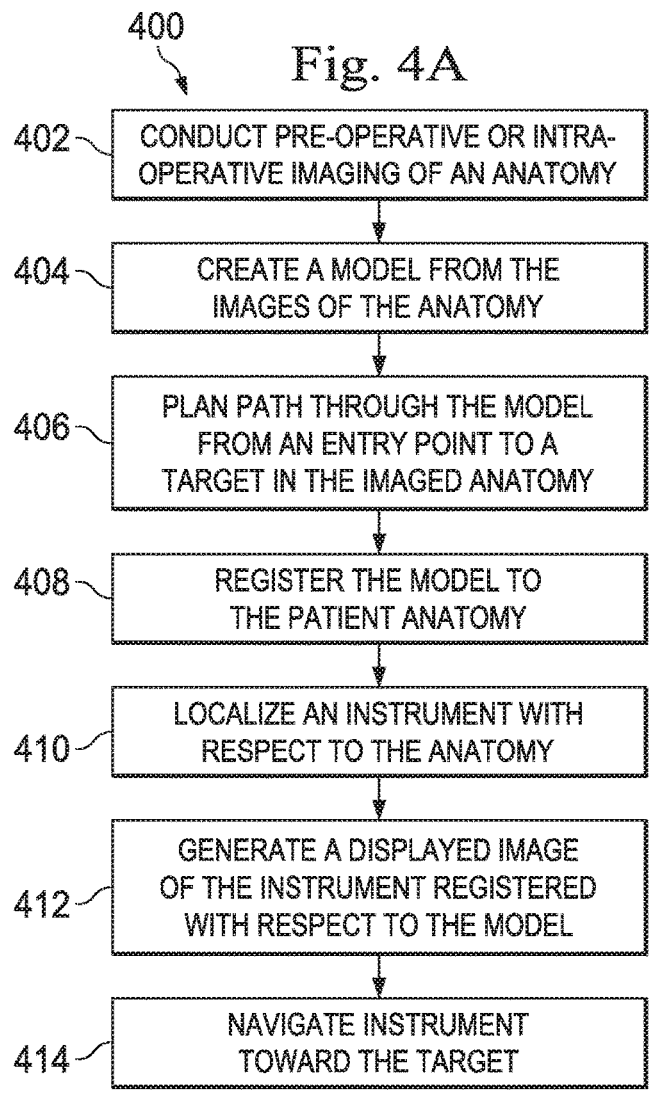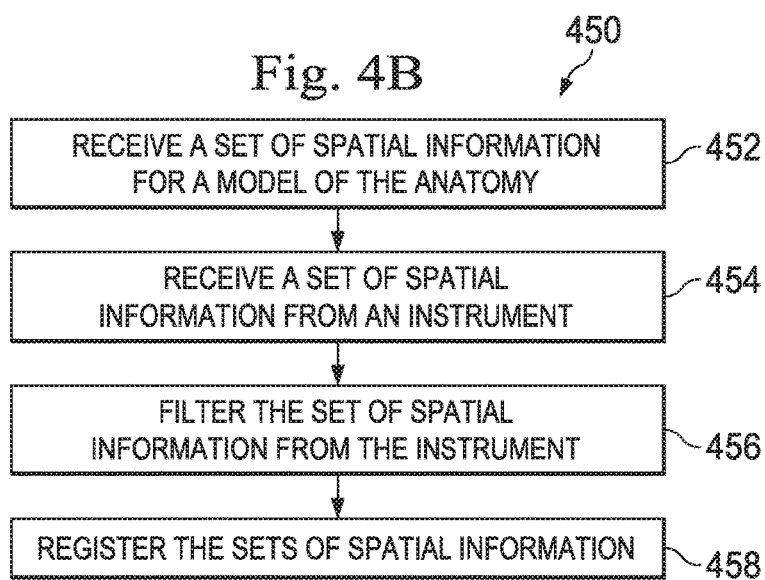

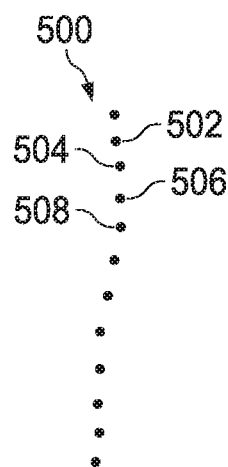
Fig. 5A
| | TIME | POSITION | ORIENTATION | WEIGHT |
|---|---|---|---|---|
| 502 | T1 | P1 | O1 | W1 |
| 504 | T2 | P2 | O2 | W2 |
| 506 | T3 | P3 | O3 | W3 |
| 508 | T4 | P4 | O4 | W4 |
Fig. 5B
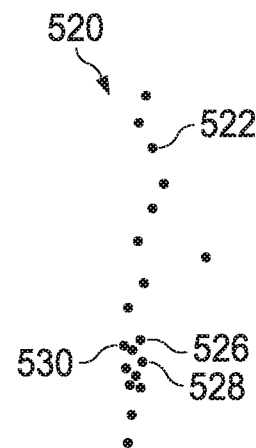
Fig. 5C

SYSTEMS AND METHODS FOR FILTERING LOCALIZATION DATA

RELATED APPLICATIONS

This patent application is a continuation application of U.S. patent application Ser. No. 15/525,909, filed May 10, 2017, which is the U.S. national phase of International Application No. PCT/US15/60083 filed Nov. 11, 2015 which claims priority to and the benefit of the filing date of U.S. Provisional Patent Application 62/079,139, entitled "SYSTEMS AND METHODS FOR FILTERING LOCALIZATION DATA," filed Nov. 13, 2014, all of which are incorporated by reference herein in their entirety.

FIELD

The present disclosure is directed to systems and methods for image guided surgery, and more particularly, to methods and systems for localizing a surgical instrument with respect to a patient anatomy.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. The instruments may navigate natural or surgically created passageways in anatomical systems such as the lungs, the colon, the intestines, the kidneys, the heart, the circulatory system, or the like. To assist with reaching the target tissue location, the position, orientation, shape, and/or movement of the medical instruments may be correlated with pre-operative or intra-operative images of the patient anatomy. The image-guided instruments may be localized with respect to the patient anatomy using, for example, electromagnetic (EM), mechanical, optical, or ultrasonic tracking systems. Generally, the accuracy of the localization is increased as more spatial information about the instrument in received. However, receiving redundant or inaccurate spatial information about the location of the instrument may reduce the accuracy of the localization or may slow the localization process. Improved techniques for filtering spatial information are needed to improve instrument localization with respect to the anatomy.

SUMMARY

The embodiments of the invention are summarized by the claims that follow below.

In one embodiment, a method performed by a computing system comprises providing instructions to a teleoperational assembly to move an instrument within an anatomic passageway according to a commanded velocity profile. The method also comprises receiving a set of spatial information from the instrument positioned within the anatomic passageway and filtering the set of spatial information to select a quantity of spatial data records from the set of spatial information proportionate to the commanded velocity profile.

In another embodiment, a method performed by a computing system comprises receiving a first set of spatial information from an instrument positioned within an anatomic passageway. The first set of spatial information includes a plurality of spatial data records including position information for a distal end of the instrument at a plurality of time periods. The method also comprises ordering the plurality of spatial data records in a time-gathered order and evaluating a spatial relationship between first and second consecutive spatial data records of the plurality of spatial data records. The method also includes filtering the first set of spatial information based upon the evaluated spatial relationship.

In another embodiment, a method performed by a computing system comprises receiving a first set of spatial information from an instrument positioned within an anatomic passageway. The first set of spatial information includes a plurality of spatial data records including position information for a distal end of the instrument at a plurality of time periods. The method also includes generating a confidence factor for each of the plurality of spatial data records and filtering the first set of spatial information based upon the generated confidence factor.

In another embodiment, a method performed by a computing system comprises receiving a first set of spatial information from an instrument positioned within an anatomic passageway. The first set of spatial information including a plurality of spatial data records includes position information for a distal end of the instrument at a plurality of time periods. The method also includes receiving shape data from a shape sensor disposed within the instrument and filtering the first set of spatial information by removing at least one of the plurality of spatial data records based upon the received shape data.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3 is a diagram showing an instrument registered to a model patient anatomy, according to one example of principles described herein.

FIG. 4A is a flowchart showing an illustrative method for performing a registration process, according to one example of principles described herein.

FIG. 4B is a flowchart showing an illustrative method for filtering spatial information.

FIG. 5A illustrates a set of spatial data records shown as data points spatially arranged to illustrate localization signals from a distal end of an instrument passing through an anatomic passageway.

FIG. 5B is a table of the spatial data records of FIG. 5A.

FIG. 5C illustrates another set of spatial data records shown as data points spatially arranged to illustrate localization signals from a distal end of an instrument passing through an anatomic passageway.

DETAILED DESCRIPTION

Figure 1:
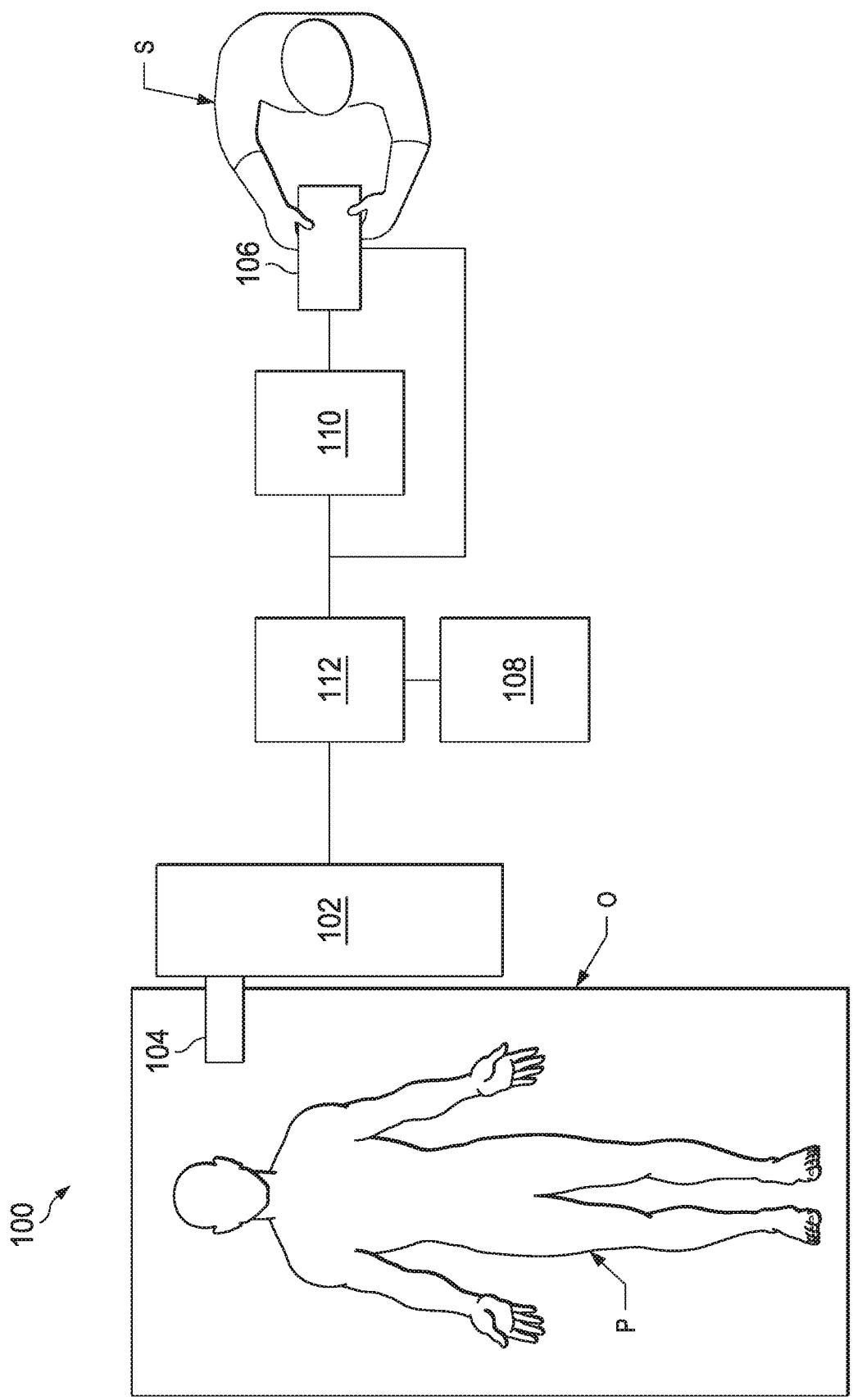
FIG. 1 is a diagram showing an illustrative teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console C, which is usually located in the same room as operating table O. However, it should be understood that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to the surgeon. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During an image-guided procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
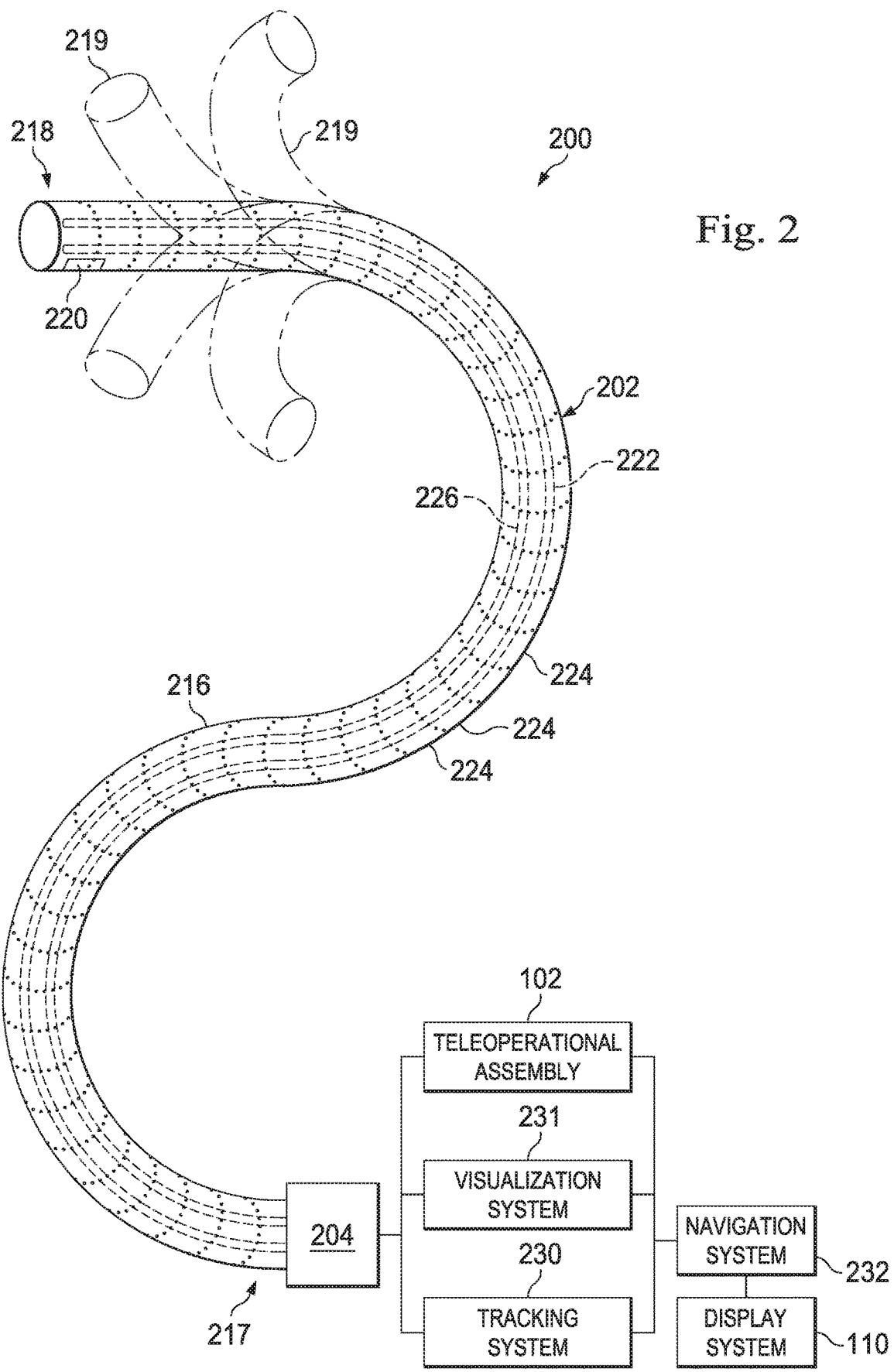
FIG. 2 is a diagram showing an illustrative medical instrument system, according to one example of principles described herein.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The optical fiber of the shape sensor 222 may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

FIG. 3 depicts a display system 150 (e.g., the display system 110) providing a composite image of an anatomic model 151 of a human lung 152, from a viewpoint external to the lung. Such an image shows an illustrative path through anatomic passageways 156 to a target location 153. The model lung 151 is registered with an instrument image 154 of a flexible instrument, such as catheter system 202.

FIG. 4A provides a flowchart 400 illustrating a process for generating a composite image such as the composite image of FIG. 3. At a process 402, a pre- or intra-operative image (e.g., CT or MRI) of the relevant portion of the patient anatomy may be obtained. At a process 404, a model of the anatomy may be generated from the set of images using a modeling function such as a segmentation process. Through either a manual and/or a computer software-based segmentation process, the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels.

At a process 406, an operator or an automated control system may plan a path through the model to a target structure or region (e.g., a tumor or an occlusion). Although not illustrated, the path planning process may occur and reoccur at various stages in the procedure 400. At a process 408, the model is registered to the patient anatomy. More specifically, the 3D surface that encloses the voxels may be dynamically referenced to the patient anatomy. The model has a frame of reference and an associated model coordinate system. The model frame of reference is registered to a patient frame of reference so that the locations of anatomic structures identified in the model can be transformed to the patient frame of reference in which the actual patient and interventional instrument exist.

At a process 410, the instrument is localized with respect to the patient anatomy. More specifically, the instrument tracking system (e.g. system 230) tracks the location of the instrument relative to the patient anatomy as the instrument moves through the anatomy. The tracking system may track the location of a portion of the tool such as a distal end of the tool. More than one location on the instrument may be tracked. At a process 412, the tracked instrument is registered with the anatomic model and, optionally, a displayed image is generated as shown in FIG. 3. More specifically, the location, orientation, shape, movement, or other spatial reference data for the interventional instrument in the patient frame of reference can be matched and transformed to the model frame of reference so that the movement of the instrument with respect to the modeled anatomic structures can be tracked and displayed. Various techniques can be used to register the position of the instrument with the model. In one example, an Iterative Closest Point (ICP) technique is used. ICP is a technique whereby a first set of spatial reference points is transformed with respect to a second set of points such that the total sum difference between corresponding points is reduced. The transformation is iteratively revised such that the two sets of points are at a minimal distance from each other. When using ICP to register data associated with a position of an instrument within an anatomy to a model of that anatomy, the first set of points corresponds to points or spatial data information that represent the model. The second set of points corresponds to points or spatial data records obtained from various types of tracking systems associated with the instrument. The spatial data records obtained from the tracking systems may provide information about the time or order in which the record was created and may include position, orientation, shape, movement or other spatial information about the instrument. As the points obtained from the instrument are updated due to movement of the instrument, the second set of points in space is iteratively transformed with respect to the first set of points from the model. Thus, the instrument stays registered with the model as the instrument navigates the passageway toward the target in process 414.

Generally, the accuracy of the instrument localization and registration is increased as more spatial information about the instrument in received. However, receiving redundant or inaccurate spatial information about the location of the instrument may reduce the accuracy of the localization or may slow the localization process. For example, inconsistent spatial data records may be obtained due to irregularities in the sensor systems of the tracking system. If these outlier data points are used to compute localization and registration, the results may be inaccurate. In another example, if spatial data records are being obtained at specific time intervals and the instrument becomes stopped, there may be an large set of spatial data records for a particular anatomical area. This can cause the ICP function to give undue weight to that area and can increase error in the registration process.

According to principles described herein, the set of spatial data records obtained from an instrument's tracking system can be filtered such that certain records are removed or given a lower weight when used for ICP or other registration techniques. Filtering may also include selecting for analysis only spatial data records that satisfy a criterion. It is understood, however, that the techniques described herein are not limited to use in registration but may be used for other purposes such as building or modifying a model by tracking movement of the instrument through the anatomic passageways. The filtering may be done in a variety of ways as will be described herein.

FIG. 4B is a flowchart showing an illustrative method 450 for performing a registration using filtered data. At an optional process 452, a set of spatial information is received from a model of the patient anatomy. This set of spatial information may include a set of elements corresponding to passageways in the patient anatomy. The elements may be represented, for example, as voxels, passageway centerline points, or a mesh model. The set of spatial information from the model may also include a three-dimensional surface that surrounds the voxels. At a process 454, a set of spatial information is obtained from the instrument tracking system. This set of spatial information may be a set of spatial data records obtained from the tracking system providing information about the time or order in which consecutive records were created and may include position, orientation, shape, movement or other spatial information about the instrument. At a process 456, the set of spatial information from the tracking system is filtered by selecting, removing, or providing a weighting factor to the spatial data records that are deemed to be redundant, outliers, of a lower confidence or quality, from an undesirable time period (e.g., too old or too new), obtained during a certain cycle of cyclic anatomical motion, associated with a deformed shape, or other reasons that may cause a particular spatial data record or subset of spatial data records to be objectionable or preferable. Optionally, at a process 458, the filtered set of spatial data records from the tracking system and the spatial information from the model may be registered. Optionally, an image of the instrument registered to the anatomy may be displayed.

FIG. 5A illustrates a set 500 of points including points in space that correspond to spatial data records 502, 504, 506, 508 obtained from an instrument (e.g. instrument system 200). FIG. 5B illustrates a table 510 of the spatial data records 502, 504, 506, 508. The spatial data records may be obtained, for example, from a sensor (e.g. an EM sensor) located on a distal portion of the instrument. Each spatial data record provides spatial information about the distal portion of the instrument at various times. For example, spatial data record 502 describes the position P1 and orientation O1 of the distal end of the instrument at a time T1. A weighting factor W1 may be associated with the spatial data record 502. The weighting factors may be applied after a filtering process is performed for the set of data. For example, a weight W1 of 1 may indicate that the spatial data record 502 is usable or not otherwise objectionable for purposes of registration. A weight W1 of 0 may indicate that the spatial data record 502 is discarded or not to be used in registration of the instrument. A weight W1 between 0 and 1 may be applied if the confidence level in the spatial data record 502 is uncertain or low. Thus, the record 502 would be considered in a registration algorithm but would not be weighted as strongly as records that had a strong confidence level and a weight of 1. A record 504 is obtained at a time T2, consecutive to the time T1, and is associated with the new position P2 and orientation O2 for the instrument. Although not shown, the spatial data record 502 may include other fields including shape data, velocity data, motor torque, force, or other spatial information for the instrument at the time T1.

In various other embodiments, a set of spatial information obtained from the instrument may include spatial data records that contribute to inaccuracies when using the full set of records for registration or model building. Various techniques for filtering spatial data records obtained from an instrument may be used in registration or modeling procedures. Any one or a combination of the filtering methods described below may be used to filter spatial data records.

Redundant Data Filtering

Figure 6A:
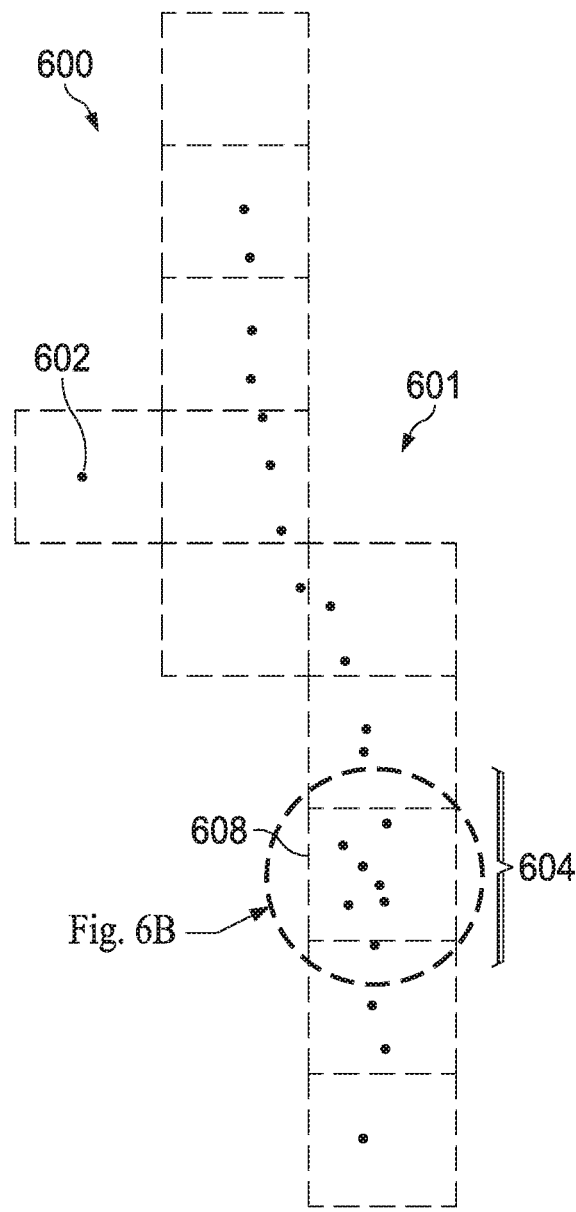
FIG. 6A illustrates a set of spatial data records shown as data points together with a segmentation map associated with the shape of an anatomic passageway.

In various embodiments, the spatial data records may be filtered by discarding or applying a reduced weighting factor records that are redundant to records that were previously obtained and that thus do not provide additional spatial information. FIG. 5C illustrates a set 520 of points in space that correspond to spatial data records including records 522, 524, 526, 528, and 530 obtained from an instrument (e.g. instrument system 200). Applying a filtering process to the set 520 may cause the records 528 and 530 to be recognized as redundant (e.g. providing the same or similar spatial information) of record 526. Redundant data records may occur when records are obtained at regular time intervals but the instrument movement has backtracked or stalled within the anatomic passageway due to, for example, instrument size (e.g. too large within a narrow passageway), an anatomic obstruction, or command errors. The records 528, 530 may therefore be weighted with a zero or a value near zero to minimize the use of those records in an instrument registration process. Redundancy may be determined in a variety of different ways. In one embodiment, redundancy may be based upon a spatial relationship between spatial data records that correspond to a variety of voxels or other spatial containers. For example, as shown in FIG. 6A, an anatomic model may be comprised of a plurality of elements represented, for example, by a set of voxels 601 (e.g. a voxel map) that correspond to an imaged and segmented anatomic passageway. Each spatial data record in a set 600 of spatial data records obtained from an instrument may be associated with or matched to a voxel in the set of voxels 601. Thus, the voxel map can be used to track which areas of three-dimensional space have been sampled to obtain spatial data records. For example, a voxel 608 in the voxel map 601 may be associated with a plurality 604 of obtained spatial data records. If the number of spatial data records associated with a single voxel exceeds a threshold value, which may be any value greater than one, the extra spatial records may be filtered by being discarded (e.g., give a weighting value of zero) or by being provided with a low weighting value (e.g., less than one). Alternatively, the weighted or unweighted spatial data records associated with the single voxel may be averaged.

Figure 6B:
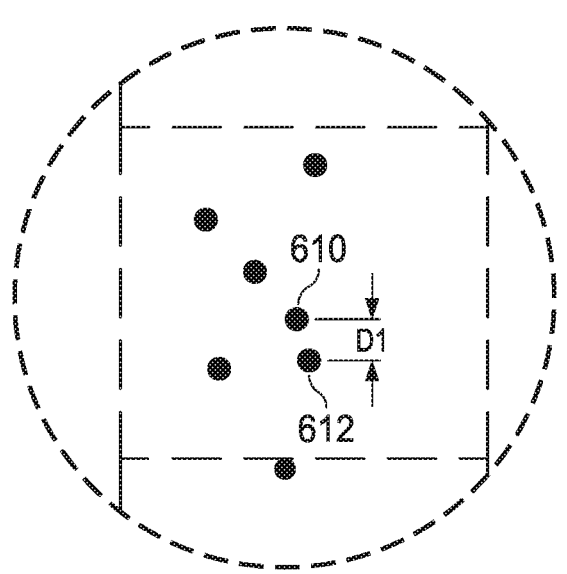
FIG. 6B illustrates a portion of the data points of FIG. 6B.

In another embodiment, redundancy may be based upon a spatial relationship such as a measured distance between the data records. For example, redundancy may be determined by ordering a plurality of spatial data records in collection time-gathered order. For example, as shown in FIG. 6B, a distance D1 between a first consecutive spatial data record 610 and a second consecutive spatial data record 612 may be measured. If the distance D1 is below a threshold value (e.g. too close), the second consecutive record 612 may be considered redundant of the first value 610. One of the first or second consecutive records, therefore, may be filtered by being discarded (e.g., give a weighting value of zero) or provided with a low weighting value (e.g., less than one). This process of evaluating consecutive records may be optimized using a k-dimensional tree analysis.

Commanded Position Filtering

Figure 7:
FIG. 7 illustrates a commanded velocity profile according to an embodiment of this disclosure.

In various embodiments, the spatial data records may be filtered by discarding, applying a reduced weighting factor, or selecting records based upon the teleoperational commanded position, orientation, or velocity of the instrument. The commanded position of the instrument provides an indicator of the expected distance to be traveled by the instrument during a particular time period. A commanded velocity may be based upon the commanded position and a commanded time period for reaching that commanded position (e.g., difference in commanded position/time period). As shown in FIG. 7, a commanded velocity profile 700 may be provided for a medical procedure using an instrument as described above. For a time period T1, the instrument is commanded to move at a velocity V1. For a time period T2, the instrument is commanded to move at a slower velocity V2. During a time period T3, the instrument may be in transition between velocities V1 and V2. The commanded velocity profile may be generated from movement of an operator input device at an operation input system (e.g., system 106). Based on the commanded velocity of the instrument, the quantity of spatial data records to be selected by the filter may be set. The filter may select a quantity of spatial data records proportionate to the commanded velocity profile. For example, if the instrument is moving quickly (e.g., V1), the quantity of spatial data records set to be selected (Q1) by the filter during the period of movement may be larger than the quantity selected (Q2) by the filter during the same period of movement if the instrument is moving slowly (e.g., V2). By way of example only, if V1 is twice the speed of V2 (V1=2*V2), Q1 may be twice the quantity of records Q2 (Q1=2*Q2). Other proportional or non-proportional relationships between the rate of movement of the instrument and the quantity of data records collected are contemplated and understood. During periods of transition T3, the filtering may continue at a proportionate rate or may be temporarily terminated until a constant velocity is reached again. In various embodiments, the commanded position filtering technique may be modified so that the filter algorithm does not select spatial data records obtained if movement of the instrument is stalled or does not select spatial data records at a particular stage of cyclic anatomical motion. For example, the instrument may be provided with a force sensor which can detect if the distal end of the instrument is in contact with tissue that may impede or prevent motion. If a signal from the force sensor indicates that the instrument has encountered an obstruction, the filter algorithm may adjust to a state in which no spatial data records are selected for use in registration or model-building. In various embodiments, instruments may be provided with force, position, orientation or other sensors that are used to detect cyclical anatomical motion (e.g., respiration, cardiac motion) or gross movements of the patient. The filtering algorithm may select spatial data records for analysis when the motion is minimized (e.g., at a full inspiration state of respiration). Similar to FIG. 7, commanded position and orientation profiles may be used filter spatial data records. Spatial data records may also be filtered based upon forces measured on the instrument and/or associated motor torques for driving movement of the instrument. For example, if the measured motor torque is greater than an expected threshold value for creating a particular pose, the data associated with the excessive motor torque may be discarded.

Outlier Filtering

Figure 8:
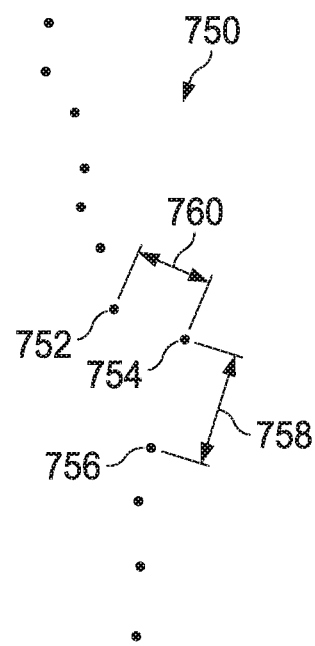
FIGS. 8-10 illustrate sets of spatial data records shown as data points spatially arranged to illustrate localization signals from a distal end of an instrument passing through an anatomic passageway.

In various embodiments, the spatial data records may be filtered by discarding, applying a reduced weighting factor, or selecting records based upon whether or not a spatial data record is identified as an outlier record. FIG. 8 illustrates a set 750 of points in space that correspond to spatial data records including records 752, 754, 756 obtained from an instrument (e.g. instrument system 200). Applying a filtering process to the set 750 may cause record 754 to become recognized as an outlier data point. An outlier point may be caused by variability in the EM sensor, cyclical anatomic motion (e.g., respiration) or other patient movement, operator steering inconsistencies, instrument characteristics such as flexibility or lack of flexibility. The record 754 may therefore be weighted with a zero or a value near zero to minimize the use of that record in an instrument registration process. The data record 754 may be identified as an outlier based upon a quality metric for the sensor (e.g., an EM sensor) that is providing the position or orientation information. Sensor quality metrics may be provide an indication of the accuracy of the sensor. For example, a six degree of freedom EM sensor may be comprised of two five degree of freedom EM sensors mounted at an angle relative to each other. If the overlapping degrees of freedom are not consistent with each other, a quality metric associated with the sensor may be determined to be low or poor. As another example, optical fiber accuracy may be a function of the tightness of the fiber bend proximate to the region of interest. If the bend is determined to be very tight, data from that region and regions distal of the bend may be discarded or discounted. Sensor noise may also be used to determine sensor accuracy for a particular time at which the data is recorded.

Additionally or alternatively, the data record 754 may be identified as an outlier based upon the distance in position or change in orientation from a predecessor or to a successor data record in view of the estimated speed of the instrument movement. For example, a distance 758 between record 754 and a subsequent consecutive record 756 and a distance 760 between record 754 and a prior consecutive record 752 may be measured. If the distances 758 and 760 are greater than an expected distance based upon the maximum velocity of the instrument, the record 754 may be identified as an outlier. Alternatively, if the distances 758 and 760 are greater than an expected distance based upon the velocity of the instrument before and after the record 754 was recorded, the record 754 may be identified as an outlier. Alternatively, if the distances 758 and 760 are greater than an average distance between other records in the set and the instrument is moving at a consistent velocity, the record 754 may be identified as an outlier. Alternatively or additionally, the orientations between the instrument for record 704 compared to preceding record 752 and subsequent record 756 may be measured. If the orientation differences are substantially different from the average orientation differences between other records in the set 750, the record 754 may be identified as an outlier.

Confidence Filtering

Figure 9:
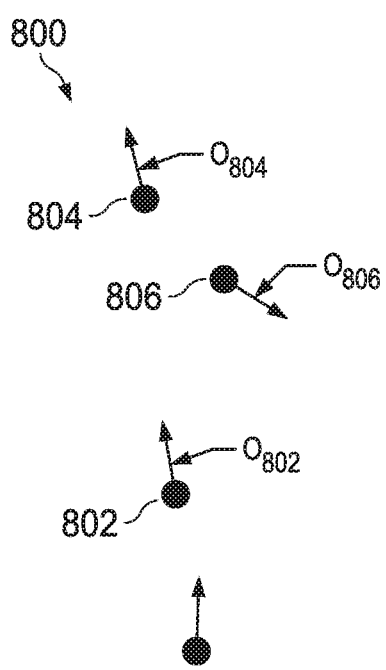

In various embodiments, the spatial data records may be filtered by discarding, applying a reduced weighting factor, or selecting records based upon a confidence value for each spatial data record. Records with low confidence values may be filtered out of the data set more aggressively. A confidence value may be determined for each spatial data record based upon an amount of variation in the signal received from the sensors or on the instrument. For example, large variations in orientation of the instrument distal end as determined from the received signal may cause the spatial data points to be given a low confidence value. If the variations in orientation of the instrument distal end are small, the spatial data points may be given a higher confidence value. As shown in FIG. 9, a set of data records 800 includes spatial data records for points 802, 804, and 806. Each spatial data record 802, 804, 806 includes an orientation value $O_{802}$, $O_{804}$, $O_{806}$, respectively. If analysis indicates that the orientation $O_{806}$ is significantly different from the previous and subsequent orientation values $O_{802}$, $O_{804}$, the data record 806 may be discarded or provided with a lower weight value.

As another example, large variations in distance (e.g., a perpendicular component of the distance) between the spatial data record and the dominant direction of travel for the instrument may cause the spatial data points to be given a low confidence value. If the variation in distance is smaller, the spatial data points may be given a higher confidence value. If confidence values for a set of spatial data records fall below a threshold value, the low confidence may be accommodated by averaging the records in the set. Confidence values may also be used with the voxel map described above. As an example, for all of the records associated with a particular element or voxel, the data records may be weighted by confidence value and the weighted records may be averaged. As another example, for all the records associated with a particular element or voxel, the orientations may be evaluated. The amount of variability may correlate to the size of the lumen of the anatomic passageway. In other words, if the variability is large, the lumen may be large because the instrument distal end is able to approach a location from multiple directions. If the variability is small, the lumen may be small because the tight passageway limits the angulation of the distal end of the instrument. Large lumens may be associated with lower confidence values. If records with low confidence values must be selected to obtain sufficient records to perform a registration process, the low confidence records may be averaged or a median record may be selected by the filter.

Temporal Filtering

Figure 10:
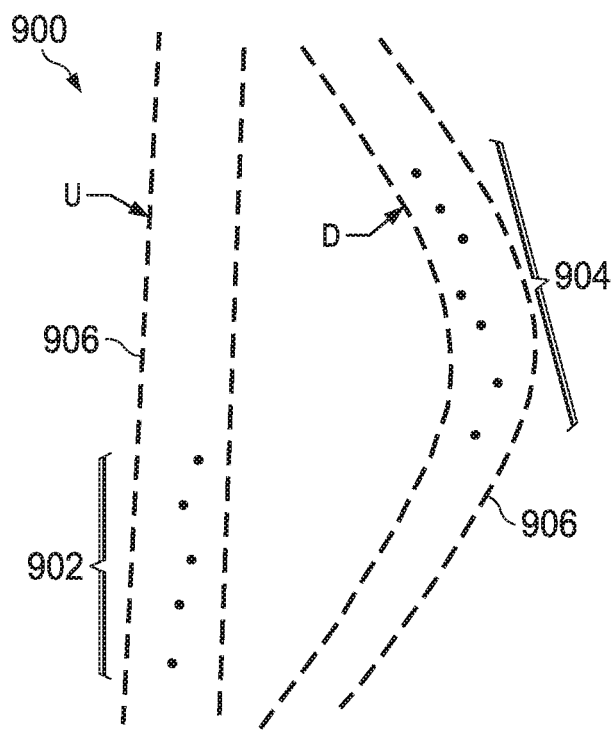
Figure 11:
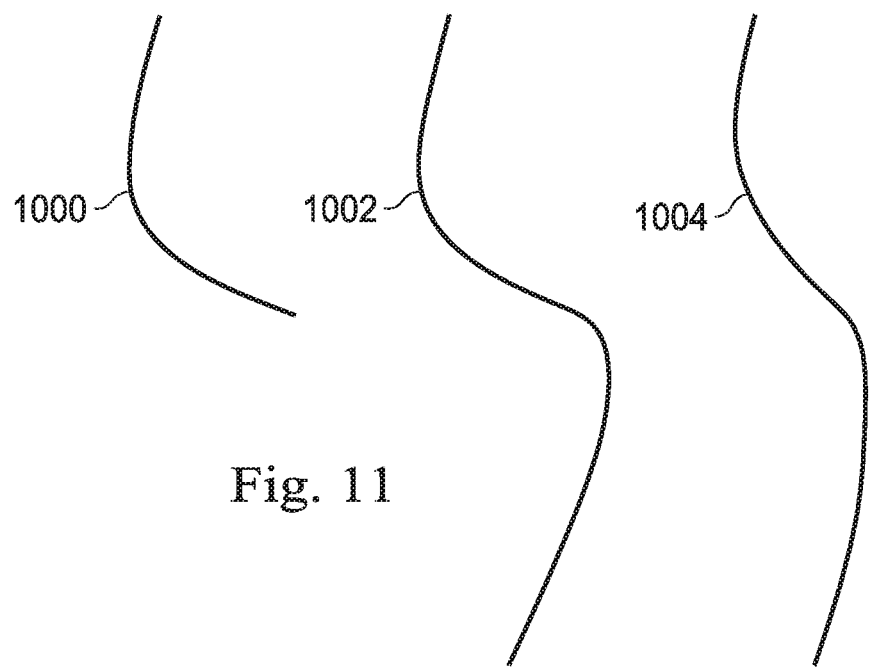
FIG. 11 illustrates a shape profiles received from a shape sensor positioned in an anatomic passageway.

In various embodiments, the spatial data records may be filtered by discarding, applying a reduced weighting factor, or selecting records based upon temporal information for each spatial data record. For example, older records (e.g., spatial data records with early time values compared to other spatial data records) may be discarded or given a lower weighting value. If the surgical procedure is likely to cause deformation, the older spatial data records from an earlier undeformed state of the anatomy may be preferred. In that case, newer records (e.g. spatial data records with later time values compared to other spatial data records) may be discarded or given a lower weighting value. As another example, spatial data records for selected times in a cyclic anatomical motion cycle (e.g., times associated with full expiration in a respiration cycle) may be selected by the filter. Alternatively, the records may be provided with weighted values based upon the amount of time that has passed since the selected time. FIG. 10 illustrates a set of spatial data records 900 including records 902 and 904. An anatomic passageway 906 is shown in an undeformed state U and a deformed state D of cyclic anatomical motion. The filtering algorithm may be set to select the record 902 for a time associated with the undeformed state rather than a record 904 for a time associated with the deformed state.

Deformation-Based Filtering

In various embodiments, the spatial data records may be filtered by discarding, applying a reduced weighting factor, or selecting records based upon whether the spatial data record is associated with anatomic deformation. This technique may be particularly suitable when using filtering to build a deformed model or determining how to register the deformed anatomy to a pre-operative, undeformed model. As shown in FIG. 10, a shape sensor extending within the instrument positioned within an anatomic passageway may return an undeformed shape profile 1000. If the anatomic passageway is undeformed by the instrument or other forces on the passageway, further advancement of the instrument and shape sensor will return a shape profile 1002 which includes the shape from the shape profile 1000. Alternatively, if the anatomic passageway is deformed by the instrument or other forces on the passageway, further advancement of the instrument and shape sensor will return a deformed shape profile 1004. The deformation of the passageway as observed by the shape profiles may be used to determine whether to filter spatial data records obtained by the instrument. For example, if a model of the undeformed anatomy is being built from the spatial data records, data records obtained while the instrument is in the deformed profile 1004 may be filtered out of the data set. If a model of the deformed anatomy is of interest, data records obtained while the instrument is in the deformed profile 104 may be preserved or selected while spatial data records associated with the shape profile 1002 may be filtered out.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The systems and methods may also be suitable for navigation around the traceable surface of an organ. The methods and embodiments of this disclosure are also suitable for non-surgical applications.

One or more elements in embodiments of the invention may be implemented in software to execute on a processor of a computer system such as control processing system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system, comprising:
   a medical instrument system;
   an assembly removably coupled to the medical instrument system and configured to operate the medical instrument system including moving the medical instrument system within an anatomic passageway;
   a sensor system coupled to the medical instrument system and configured to generate information including spatial data and shape data about the medical instrument system; and
   a control system communicatively coupled to the medical instrument system, the assembly, and the sensor system and configured to perform operations including:
      receive, from the sensor system, a first set of the spatial data including position information for a distal end of the medical instrument system during a plurality of time periods;
      receive, from the sensor system, the shape data; and
      filter the first set of the spatial data including removing at least a portion of the spatial data based on the shape data indicating a deformed state of the anatomic passageway.

2. The medical system of claim 1, wherein the control system is configured to remove the portion of the spatial data based on the portion of the spatial data being associated with a deformed shape profile of the shape data indicating the deformed state.

3. The medical system of claim 1, wherein the control system is configured to remove the portion of the spatial data based on the portion of the spatial data being associated with an undeformed shape profile of the shape data.

4. The medical system of claim 1, wherein the control system is further configured to:
   receive a second set of spatial information from a model of the anatomic passageway; and register the filtered first set of the spatial data to the second set of spatial information.

5. The medical system of claim 4, wherein the second set of spatial information includes a plurality of voxels corresponding to the anatomic passageway.

6. The medical system of claim 4, wherein the second set of spatial information includes a voxel map associated with the anatomic passageway, and wherein the control system is further configured to:

evaluate a spatial relationship between a first spatial data record of the first set of the spatial data and a second spatial data record of the first set of the spatial data, wherein the second spatial data record is temporally-consecutive to the first spatial data record, including associating each of the first and second spatial data records with a voxel in the voxel map.

7. The medical system of claim 6, wherein the control system is configured to filter the first set of the spatial data by removing at least a second portion of the spatial data based on the evaluated spatial relationship.

8. The medical system of claim 7, wherein the control system is configured to remove at least the second portion of the spatial data including track a quantity of spatial data records from the first set of the spatial data that corresponds to each voxel in the voxel map.

9. The medical system of claim 8, wherein the control system is configured to filter the first set of spatial data including average the quantity of spatial data records for each voxel in the voxel map.

10. The medical system of claim 6, wherein the spatial relationship is a distance and the control system is configured to filter the first set of spatial data including:

determine if the distance is below a distance threshold value; and remove one of the first or second spatial data records if the distance is below the distance threshold value.

11. The medical system of claim 6, wherein the spatial relationship is a distance and the control system is configured to filter the first set of spatial data including:

determine if the distance is greater than a distance threshold value; and remove one of the first or second spatial data records if the distance is above the distance threshold value.

12. The medical system of claim 6, wherein the spatial relationship is a distance and a distance threshold value for comparison with the distance is determined from a known maximum speed of the medical instrument system.

13. The medical system of claim 6, wherein the spatial relationship is a distance and a distance threshold value for comparison with the distance is determined from a known speed of the medical instrument system both before and after the second spatial data record is obtained.

14. The medical system of claim 1, wherein the spatial data includes position information.

15. The medical system of claim 1, wherein the spatial data includes orientation information.

16. The medical system of claim 1, wherein the spatial data is received from an electromagnetic sensor on the medical instrument system.

17. The medical system of claim 1, wherein the control system is further configured to render an image of the medical instrument system based on the filtered first set of the spatial data on a common display with an image of the anatomic passageway.

18. The medical system of claim 1, wherein the control system is configured to filter the first set of the spatial data including remove at least one spatial data record from the first set of the spatial data.

19. The medical system of claim 1, wherein the control system is configured to filter the first set of the spatial data including weight at least one spatial data record of the first set of the spatial data differently than another spatial data record of the first set of the spatial data.

20. A non-transitory computer-readable medium for a medical system, the non-transitory computer-readable medium containing computer executable instructions that, when executed by a processor, cause the medical system to perform a method comprising:

move a medical instrument system positioned at least partly within an anatomic passageway;

receive a first set of spatial data from the medical instrument system, the first set of spatial data including a plurality of spatial data records including position information for a distal end of the medical instrument system at a plurality of time periods;

receive shape data from a shape sensor disposed within the medical instrument system; and filter the first set of spatial data by removing at least one of the plurality of spatial data records based upon the received shape data indicating a deformed state of the anatomic passageway.

* * * * *